(12) United States Patent
Shah et al.

(10) Patent No.: US 8,205,619 B2
(45) Date of Patent: Jun. 26, 2012

(54) METHOD OF PREVENTING ARTICULATION IN A SURGICAL INSTRUMENT

(75) Inventors: Sachin Shah, Milford, CT (US); Frank C. Maffei, Shelton, CT (US)

(73) Assignee: Tyco Healthcare Group LP, Mansfield, MA (US)

( * ) Notice: Subject to any disclaimer, the term of this patent is extended or adjusted under 35 U.S.C. 154(b) by 119 days.

(21) Appl. No.: 12/721,160

(22) Filed: Mar. 10, 2010

(65) Prior Publication Data

US 2010/0163597 A1    Jul. 1, 2010

Related U.S. Application Data

(62) Division of application No. 11/863,653, filed on Sep. 28, 2007, now Pat. No. 7,703,653.

(51) Int. Cl.
*A61B 17/068* (2006.01)
(52) U.S. Cl. ........................................ 128/898
(58) Field of Classification Search ............... 227/175.2, 227/175.1, 179.1, 19; 128/898
See application file for complete search history.

(56) References Cited

U.S. PATENT DOCUMENTS

| | | | |
|---|---|---|---|
| 3,572,067 A * | 3/1971 | Kimberlin et al. ............ 70/252 |
| 3,595,039 A * | 7/1971 | Juy ................................. 70/252 |
| 3,638,462 A * | 2/1972 | White et al. ................... 70/186 |
| 3,703,092 A * | 11/1972 | Elliott ............................ 70/248 |
| 4,566,620 A | 1/1986 | Green et al. | |
| 4,728,020 A | 3/1988 | Green et al. | |
| 4,742,817 A | 5/1988 | Kawashima et al. | |
| 4,856,518 A | 8/1989 | McFadden | |
| 4,869,414 A | 9/1989 | Green et al. | |
| 4,880,015 A | 11/1989 | Nierman | |
| 4,903,697 A | 2/1990 | Resnick et al. | |
| 4,935,026 A | 6/1990 | McFadden | |
| 5,209,747 A | 5/1993 | Knoepfler | |
| 5,217,472 A | 6/1993 | Green et al. | |
| 5,219,111 A | 6/1993 | Bilotti et al. | |
| 5,258,008 A | 11/1993 | Wilk | |
| 5,271,543 A | 12/1993 | Grant et al. | |
| 5,312,023 A | 5/1994 | Green et al. | |
| 5,318,008 A | 6/1994 | Bullard | |
| 5,318,528 A | 6/1994 | Heaven et al. | |
| 5,326,013 A | 7/1994 | Green et al. | |

(Continued)

FOREIGN PATENT DOCUMENTS

EP    0832605 A    4/1997

(Continued)

OTHER PUBLICATIONS

European Search Report for EP 08253122.9-2310 date of completion is Nov. 26, 2008 (3 pages).

*Primary Examiner* — Brian D Nash

(57) ABSTRACT

An articulating elongate surgical instrument includes a handle assembly, an elongated body portion, a tool assembly pivotally supported on the distal end of the elongated body portion. The elongate surgical instrument includes as well an articulation mechanism to effect the movement of the tool assembly, the articulation mechanism including a pivot member operatively coupled to the tool assembly. The elongated body includes at least one articulation drive member having at least one retaining surface therein; a firing rod disposed adjacent the articulation drive, with an articulation locking actuating surface disposed upon the firing rod; and an articulation locking means configured to selectively engage and disengage from the actuating surface and to selectively engage and disengage from the retaining surface of the articulation drive member.

9 Claims, 15 Drawing Sheets

U.S. PATENT DOCUMENTS

| | | |
|---|---|---|
| 5,330,502 A | 7/1994 | Hassler et al. |
| 5,348,259 A | 9/1994 | Blanco et al. |
| 5,370,650 A | 12/1994 | Tovey et al. |
| 5,374,277 A | 12/1994 | Hassler |
| 5,381,943 A | 1/1995 | Allen et al. |
| 5,383,888 A | 1/1995 | Zvenyatsky et al. |
| 5,403,342 A | 4/1995 | Tovey et al. |
| 5,405,344 A | 4/1995 | Williamson et al. |
| 5,409,498 A | 4/1995 | Braddock et al. |
| 5,417,203 A | 5/1995 | Tovey et al. |
| 5,423,471 A | 6/1995 | Mastri et al. |
| 5,431,323 A | 7/1995 | Smith et al. |
| 5,439,156 A | 8/1995 | Grant et al. |
| 5,452,836 A | 9/1995 | Huitema et al. |
| 5,456,401 A | 10/1995 | Green et al. |
| 5,465,894 A | 11/1995 | Clark et al. |
| 5,478,003 A | 12/1995 | Green et al. |
| 5,482,197 A | 1/1996 | Green et al. |
| 5,485,952 A | 1/1996 | Foritayne |
| 5,490,819 A | 2/1996 | Nicholas et al. |
| 5,501,654 A | 3/1996 | Failla et al. |
| 5,514,157 A | 5/1996 | Nicholas et al. |
| 5,547,117 A | 8/1996 | Hamblin et al. |
| 5,549,636 A | 8/1996 | Li |
| 5,549,637 A | 8/1996 | Crainich |
| 5,560,532 A | 10/1996 | DeFonzo et al. |
| 5,562,682 A | 10/1996 | Oberlin et al. |
| 5,564,615 A | 10/1996 | Bishop et al. |
| 5,569,263 A | 10/1996 | Hem |
| 5,575,799 A | 11/1996 | Bolanos et al. |
| 5,577,654 A | 11/1996 | Bishop |
| 5,580,067 A | 12/1996 | Hamblin et al. |
| 5,582,617 A | 12/1996 | Klieman et al. |
| 5,582,618 A | 12/1996 | Chin et al. |
| 5,588,580 A | 12/1996 | Paul et al. |
| 5,588,581 A | 12/1996 | Conlon et al. |
| 5,601,224 A | 2/1997 | Bishop et al. |
| 5,603,443 A | 2/1997 | Clark et al. |
| 5,605,273 A | 2/1997 | Hamblin et al. |
| 5,607,094 A | 3/1997 | Clark et al. |
| 5,609,601 A | 3/1997 | Kolesa et al. |
| 5,626,553 A | 5/1997 | Frassica et al. |
| 5,630,832 A | 5/1997 | Giordano et al. |
| 5,632,432 A | 5/1997 | Schulze et al. |
| 5,665,105 A | 9/1997 | Furnish et al. |
| 5,669,544 A | 9/1997 | Schulze et al. |
| 5,673,840 A | 10/1997 | Schulze et al. |
| 5,673,841 A | 10/1997 | Schulze et al. |
| 5,674,230 A | 10/1997 | Tovey et al. |
| 5,680,982 A | 10/1997 | Schulze et al. |
| 5,692,668 A | 12/1997 | Schulze et al. |
| 5,702,408 A | 12/1997 | Wales et al. |
| 5,704,534 A | 1/1998 | Huitema et al. |
| 5,704,898 A | 1/1998 | Kokish |
| 5,713,505 A | 2/1998 | Huitema |
| 5,725,536 A | 3/1998 | Oberlin et al. |
| 5,732,871 A | 3/1998 | Clark et al. |
| 5,749,602 A | 5/1998 | Delaney et al. |
| 5,766,196 A | 6/1998 | Griffiths |
| 5,794,834 A | 8/1998 | Hamblin et al. |
| 5,797,538 A | 8/1998 | Heaton et al. |
| 5,797,939 A | 8/1998 | Yoon |
| 5,797,958 A | 8/1998 | Yoon |
| 5,797,959 A | 8/1998 | Castro et al. |
| 5,813,813 A | 9/1998 | Daum et al. |
| 5,817,119 A | 10/1998 | Klieman et al. |
| 5,820,009 A | 10/1998 | Melling et al. |
| 5,823,066 A | 10/1998 | Huitema et al. |
| 5,826,776 A | 10/1998 | Schulze et al. |
| 5,829,662 A | 11/1998 | Allen et al. |
| 5,836,960 A | 11/1998 | Kolesa et al. |
| 5,843,097 A | 12/1998 | Mayenberger et al. |
| 5,855,311 A | 1/1999 | Hamblin et al. |
| 5,865,361 A | 2/1999 | Milliman et al. |
| 5,901,895 A | 5/1999 | Heaton et al. |
| 5,951,575 A | 9/1999 | Bolduc et al. |
| 5,972,012 A | 10/1999 | Ream et al. |
| 5,976,074 A | 11/1999 | Moriyama |
| 6,066,150 A | 5/2000 | Gonon |
| 6,152,894 A | 11/2000 | Kubler |
| 6,241,139 B1 | 6/2001 | Milliman et al. |
| 6,250,532 B1 | 6/2001 | Green et al. |
| 6,330,965 B1 | 12/2001 | Milliman et al. |
| 6,450,948 B1 | 9/2002 | Matsuura et al. |
| 6,475,140 B1 | 11/2002 | Konstorum et al. |
| 6,490,467 B1 | 12/2002 | Bucholz et al. |
| 6,554,844 B2 | 4/2003 | Lee et al. |
| 6,569,105 B1 | 5/2003 | Kortenbach et al. |
| 6,589,200 B1 | 7/2003 | Schwemberger et al. |
| 6,607,475 B2 | 8/2003 | Doyle et al. |
| 6,632,170 B1 | 10/2003 | Bohanan et al. |
| 6,644,532 B2 | 11/2003 | Green et al. |
| 6,676,668 B2 | 1/2004 | Mercereau et al. |
| 6,695,781 B2 | 2/2004 | Rabiner et al. |
| 6,786,382 B1 | 9/2004 | Hoffman |
| 6,830,174 B2 | 12/2004 | Hillstead et al. |
| 6,837,887 B2 | 1/2005 | Woloszko et al. |
| 6,872,214 B2 | 3/2005 | Sonnenschein et al. |
| 6,877,647 B2 | 4/2005 | Green et al. |
| 6,942,613 B2 | 9/2005 | Ewers et al. |
| 6,960,163 B2 | 11/2005 | Ewers et al. |
| 6,964,363 B2 | 11/2005 | Wales et al. |
| 6,981,628 B2 | 1/2006 | Wales |
| 7,001,400 B1 | 2/2006 | Modesitt et al. |
| 7,055,731 B2 | 6/2006 | Shelton, IV et al. |
| 7,087,071 B2 | 8/2006 | Nicholas et al. |
| 7,097,089 B2 | 8/2006 | Marczyk |
| 7,101,372 B2 | 9/2006 | Dycus et al. |
| 7,101,373 B2 | 9/2006 | Dycus et al. |
| 7,108,703 B2 | 9/2006 | Danitz et al. |
| 7,111,769 B2 | 9/2006 | Wales et al. |
| 7,278,563 B1 | 10/2007 | Green |
| 2005/0006430 A1* | 1/2005 | Wales .................. 227/175.1 |
| 2006/0025809 A1 | 2/2006 | Shelton |
| 2006/0069396 A1 | 3/2006 | Meade et al. |
| 2006/0190034 A1 | 8/2006 | Nishizawa et al. |
| 2007/0027468 A1 | 2/2007 | Wales et al. |

FOREIGN PATENT DOCUMENTS

| | | |
|---|---|---|
| EP | 1 813 203 A2 | 8/2007 |
| WO | WO03/030743 A | 4/2003 |

* cited by examiner

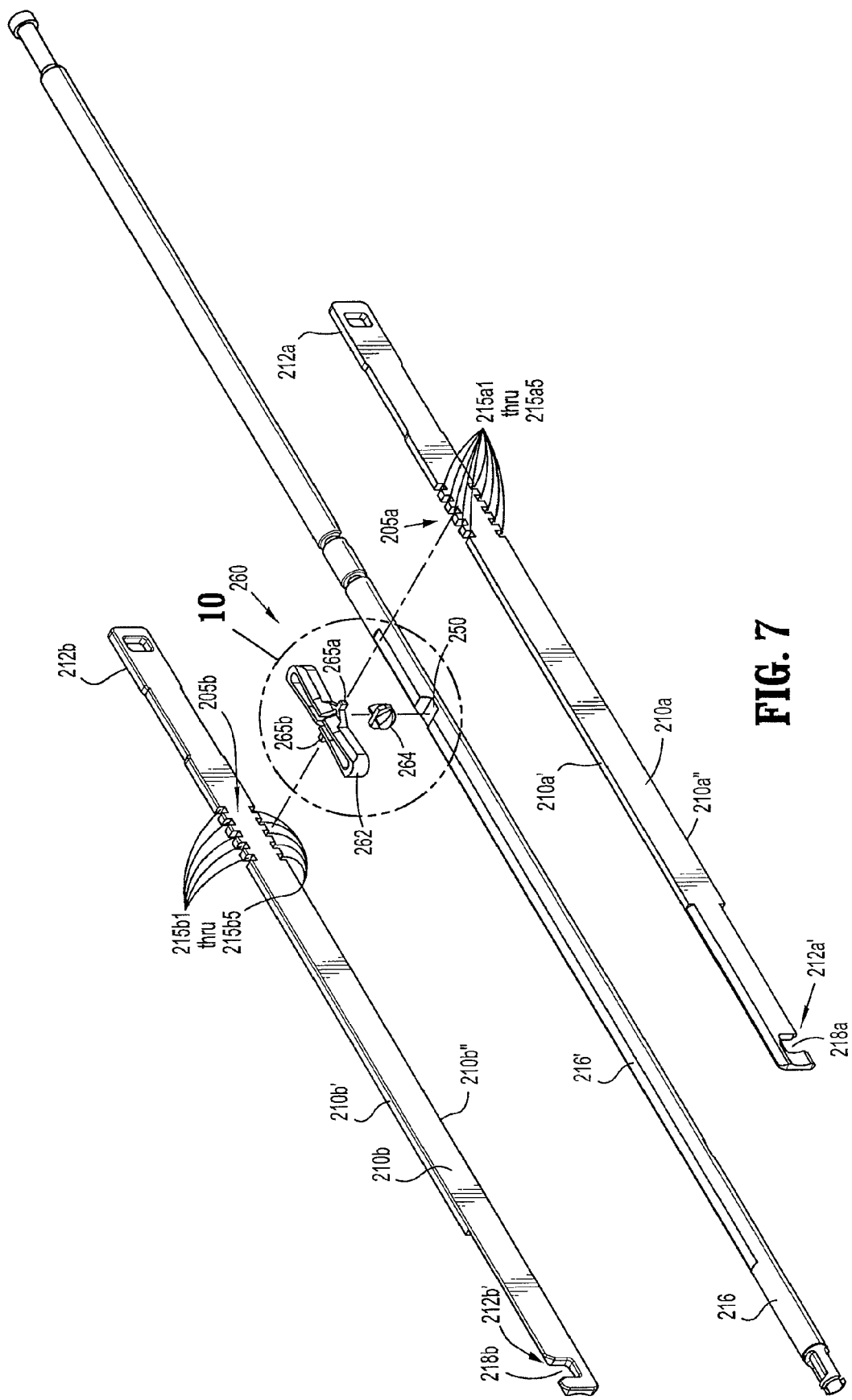

METHOD OF PREVENTING ARTICULATION IN A SURGICAL INSTRUMENT

CROSS-REFERENCE TO RELATED APPLICATIONS

This application is a divisional of U.S. patent application Ser. No. 11/863,653 by Shah et al. entitled "ARTICULATION MECHANISM FOR SURGICAL INSTRUMENT", filed Sep. 28, 2007, now U.S. Pat. No. 7,703,653 issued on Apr. 27, 2010, and each of which are hereby incorporated by reference in their entirety.

BACKGROUND

1. Technical Field

This application relates to a mechanism to effect movement of at least a portion of a surgical instrument, and more particularly, to an articulating mechanism for use with an elongate surgical instrument.

2. Background of Related Art

Surgical devices wherein tissue is first grasped or clamped between opposing jaw structure and then joined by surgical fasteners are well known in the art. In some instruments a knife is provided to cut the tissue which has been joined by the fasteners. The fasteners are typically in the form of surgical staples but two part polymeric fasteners can also be utilized.

A stapler disclosed in U.S. Pat. No. 3,499,591 applies a double row of staples on each side of the incision. This is accomplished by providing a disposable loading unit in which a cam member moves through an elongate guide path between two sets of staggered staple carrying grooves. Staple drive members are located within the grooves and are positioned in such a manner so as to be contacted by the longitudinally moving cam member to effect ejection of the staples from the staple cartridge of the disposable loading unit. Other examples of such staplers are disclosed in U.S. Pat. Nos. 4,429,695 and 5,065,929.

Each of the instruments described above were designed for use in conventional surgical procedures wherein surgeons have direct manual access to the operative site. However, in endoscopic or laparoscopic procedures, surgery is performed through a small incision or through a narrow cannula inserted through small entrance wounds in the skin. In order to address the specific needs of endoscopic and/or laparoscopic surgical procedures, endoscopic surgical stapling devices have been developed and are disclosed in, for example, U.S. Pat. No. 5,040,715 (Green, et al.); U.S. Pat. No. 5,307,976 (Olson, et al.); U.S. Pat. No. 5,312,023 (Green, et al.); U.S. Pat. No. 5,318,221 (Green, et al.); U.S. Pat. No. 5,326,013 (Green, et al.); and U.S. Pat. No. 5,332,142 (Robinson, et al.).

Certain current laparoscopic linear staplers are configured to operate in an articulated off axis configuration. Samples of articulating endoscopic surgical staplers are disclosed in U.S. Pat. No. 6,953,139 issued to Milliman et al.

SUMMARY

The present disclosure relates to an articulating elongate surgical instrument that includes a handle assembly, and an elongated body portion extending distally from the handle assembly and defining a first longitudinal axis. The elongate surgical instrument also includes a tool assembly pivotally supported on the distal end of the elongated body portion about a pivot axis substantially orthogonal to the first longitudinal axis. The elongate surgical instrument includes as well an articulation mechanism to effect the movement of the tool assembly.

The instrument has at least one articulation drive member with at least one retaining surface; a rod disposed adjacent the at least one articulation drive member, with an actuating surface disposed upon the rod; and an articulation locking assembly configured to selectively engage and disengage the actuating surface and to selectively engage and disengage from the at least one retaining surface of the at least one articulation drive member.

The at least one articulation drive member can include two articulation drive members, each of the two articulation drive members having at least one retaining surface for engagement and disengagement by the articulation locking assembly. The articulation locking assembly can have at least two retaining surfaces, at least one of the retaining surfaces engaging one of the two articulation drive members, and at least the other of the retaining surfaces engaging the other of the two articulation drive members.

The retaining surface or surfaces of the articulation locking assembly may be configured as one or more protrusions. The protrusions may selectively engage and disengage from the respective at least one retaining surface of the articulation drive member. The at least one retaining surface of the articulation drive members may be configured as channels receiving the respective protrusions of the articulation locking assembly.

The at least one retaining surface of the articulation locking assembly may each include a frictional surface. The at least one retaining surface of the articulation drive member or members may include a frictional surface.

In one embodiment, the articulation locking assembly may include a flexible member that is expansible laterally. The articulation locking assembly may further include a motive member movable toward the flexible member. The actuating surface disposed upon the rod may be configured as a detent channel in a surface of the rod. The detent channel may include at least one ramp surface configured to urge movement of the motive member upon motion of the rod.

In one embodiment, the flexible member may have an interior space and wherein, upon motion of the rod, the motive member enters the interior space of the flexible member and expands the flexible member laterally. The motive member may have an inclined surface for engaging the flexible member.

The flexible member may be configured with sufficient resiliency to urge the motive member away from the flexible member and to release thereby the drive members to allow movement of the drive members. The flexible member may include at least a pair of inclined surfaces spanning the interior space, and the motive member may be configured wherein motion of the motive member to engage the inclined surfaces of the flexible member causes the retaining surfaces of the flexible member to engage with, or disengage from, the retaining surface of the respective articulation drive members. The flexible member may further include an aperture, and the motive member may further include a protrusion configured to lockingly engage with and to be received by the aperture of the flexible member. The protrusion of the motive member may lockingly engage with and be received by the aperture of the flexible member during motion of the motive member to engage the inclined surfaces of the flexible member to cause the retaining surfaces of the articulation locking means to selectively engage and disengage from the retaining surface of the respective articulation drive members.

In one embodiment, the elongated body portion includes at least two drive members each having at least two retaining surfaces, an operating lever, and a base plate. The base plate may be operatively coupled to the operating lever, with the base plate having first and second pairs each of a distal engaging portion and a proximal engaging portion. The first pair of distal engaging portions may be configured to alternately engage the distal engaging apertures upon movement of the operating lever, while the second pair of proximal engaging portions may be configured to alternately engage the proximal engaging apertures upon movement of the operating lever.

The base plate may further include a plurality of notches, wherein each of the plurality of notches corresponds to a particular position of the base plate effecting a particular position of articulation of the pivot member, and the surgical instrument further includes a locking actuator lockingly engaging with any one of the plurality of notches in the base plate to lock a particular position of articulation of the pivot member.

The rod of the instrument may comprise a firing rod for effecting the firing of surgical staples from the tool assembly.

In a further aspect of the present disclosure, a method of preventing articulation in a surgical instrument includes moving a rod having an actuating surface thereon, so that the actuating surface engages an articulation locking assembly. the articulation locking assembly has a flexible member that is cammed laterally to engage at least one articulation drive member. The method can include that the motive member is engaged with the rod, the actuating surface urging movement of the motive member. The motive member may be moved toward the flexible member. In certain embodiments, the motive member moves into an interior space of the flexible member, expanding the flexible member laterally. The method can include moving the motive member into a channel in the rod and away from the flexible member. Retaining surfaces on the flexible member can be moved into engagement with retaining surfaces on the at least one articulation drive member.

In certain embodiments, the flexible member is cammed laterally in two directions to engage two articulation drive members. The motive member can slide along at least one inclined surface. In a preferred embodiment, surgical staples are fired from the surgical instrument, including moving the rod in a distal direction.

BRIEF DESCRIPTION OF THE DRAWINGS

Various embodiments are described herein with reference to the drawings:

FIG. 7 is a perspective view with parts separated of the internal components of the elongated body portion of the elongate surgical instrument of FIG. 6;

DETAILED DESCRIPTION

Figure 1:
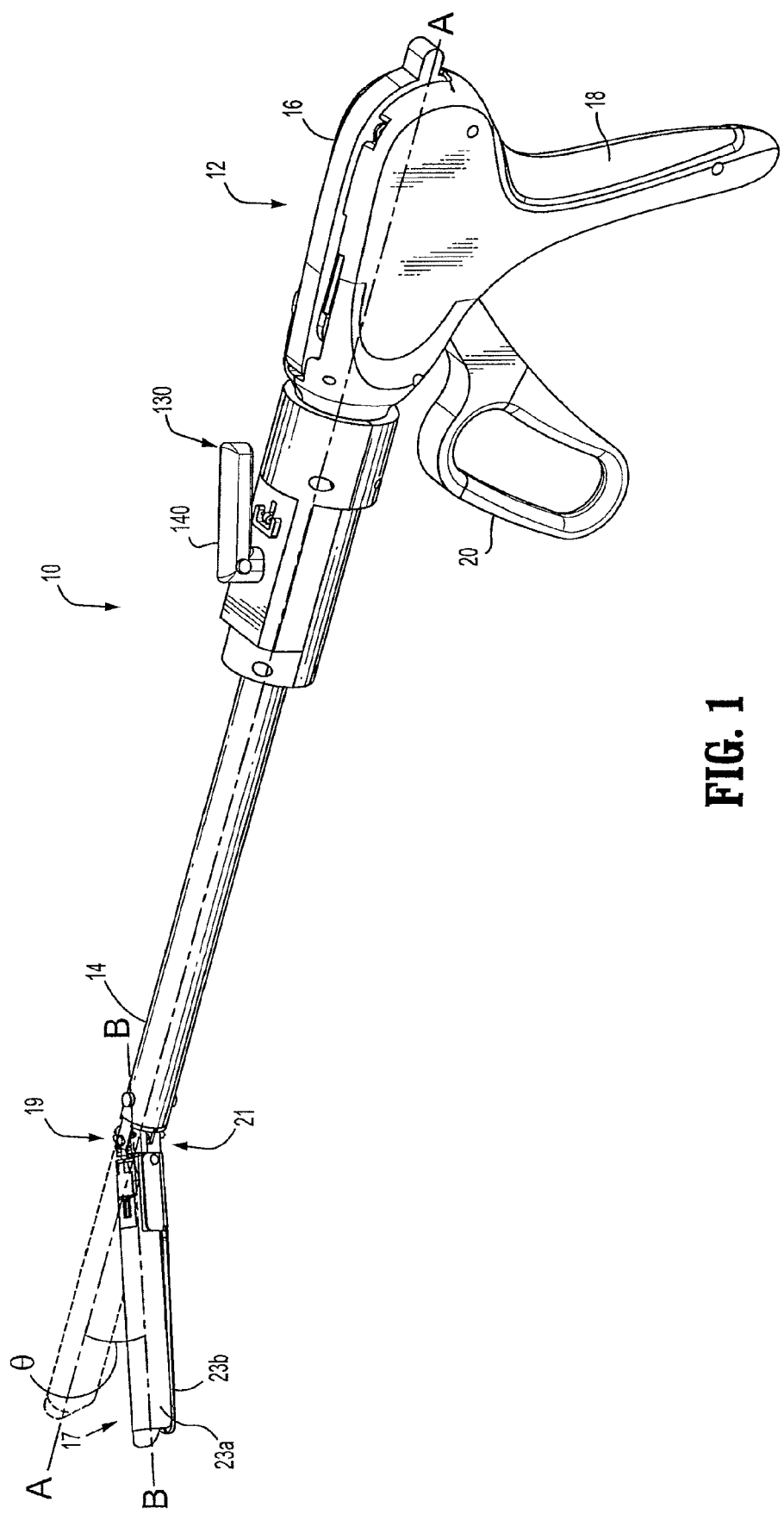
FIG. 1 is a perspective view of an embodiment of the presently disclosed surgical stapling apparatus.

Embodiments of the present disclosure will now be described in detail with reference to the drawings, in which like reference numerals designate identical or corresponding elements in each of the several views.

In the drawings and in the description that follows, the term "proximal", as is traditional, will refer to the end or portion of the surgical instrument which is closest to the operator, while the term distal will refer to the end or portion of the surgical instrument which is furthest from the operator.

Figure 2:
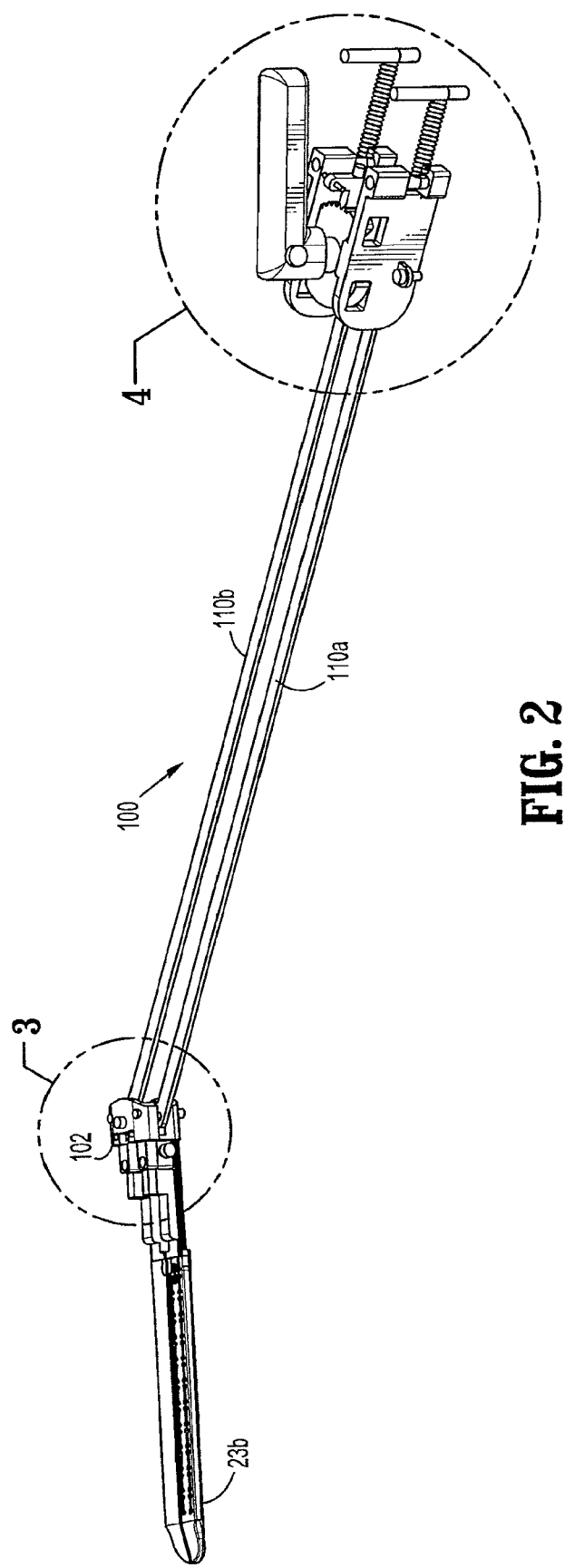
FIG. 2 is a perspective view of the articulation mechanism of the surgical apparatus shown in FIG. 1.

Referring now to FIGS. 1-5, an elongate surgical instrument, e.g. a surgical stapling apparatus for applying surgical staples, according to the present disclosure is shown generally as surgical instrument 10. Surgical instrument 10 generally includes a handle assembly 12 having a housing 16 with a handle portion 18 and a movable trigger portion 20. The surgical instrument 10 includes an elongated body 14 operatively coupled to the housing 16. An articulation lever 130 is also mounted on the forward end of handle assembly 12 to facilitate articulation of tool assembly 17. In one embodiment, tool assembly 17 is releasably secured to a distal end 19 of elongated body 14. As illustrated in FIGS. 1-2, the tool assembly 17 has a pair of jaws 23a and 23b including an anvil assembly 23a and a cartridge assembly 23b. The anvil assembly 23a is movably secured in relation to elongated body 14. The anvil assembly 23a is disposed in opposition to the cartridge assembly 23b and the cartridge assembly 23b is configured to apply linear rows of staples. Replaceable loading units with tool assemblies for applying rows of staples measuring from about 30 mm to about 60 mm in length may be connected to the distal end 19 of elongated body 140. Replaceable loading units having linear rows of staples of other lengths are also envisioned, e.g., 45 mm. The deployment of the surgical staples and the actuation mechanism therefor is disclosed in U.S. Patent Application Publication No. 2004/0232201 A1, the entire disclosure of which is hereby incorporated by reference herein.

The general overall arrangement, construction and operation of surgical instrument 10 embodied as an endoscopic surgical stapling apparatus is similar in many respects to a surgical stapling apparatus such as, for example but not limited to, that described in more detail in commonly assigned U.S. Pat. No. 6,953,139 B2, by Milliman et al, published Oct. 11, 2005, the entire contents of which is hereby incorporated by reference herein. The surgical instrument 10 may also be embodied as a grasping instrument, a retractor or as another instrument requiring articulation of a surgical tool member. The embodiments are not limited to the context of an endoscopic surgical stapler.

In an embodiment according to the present disclosure, the surgical instrument 10 further includes an articulation mechanism 100 (see FIG. 2) to effect the movement of the tool assembly 17. The articulation mechanism 100 includes a pivot member 102 that is operatively coupled to the tool assembly 17 at a proximal end 21 thereof (see FIG. 1). The elongated body portion 14 extends distally from the handle assembly 12 and defines a first longitudinal axis. The tool assembly 17 is pivotally supported by the pivot member 102 on the distal end of the elongated body portion 14 about a pivot axis defined by the pivot member 102 that is substantially orthogonal to the first longitudinal axis. The tool assembly 17 defines a second longitudinal axis and is movable between a first position in which the second longitudinal axis is aligned with the first longitudinal axis to a second position in which the second longitudinal axis is positioned at an angle to the first longitudinal axis.

The articulation mechanism 100 is further configured with at least first and second articulation drive members 110a and 110b, respectively, that are operatively coupled to the pivot member 102 such that relative motion of the first articulation drive member 110a with respect to the second articulation drive member 110b moves the pivot member 102 to effect the movement of the tool assembly 17.

The articulation mechanism 100 may further include an actuation assembly 104. The actuation assembly 104 includes at least first and second articulation drive plates 112a and 112b, respectively. The first articulation drive plate 112a may be operatively coupled to at least the first articulation drive member 110a, while at least the second articulation drive plate 112b may be operatively coupled to at least the second articulation drive member 110b, such that relative motion of one of the first and second articulation drive plates 112a or 112b, respectively, with respect to another one of the first and second articulation drive plates 112b or 112a, respectively, moves the pivot member 102 to effect the movement of the tool assembly 17. In one embodiment, the drive members 110a and 110b may be formed of strips or bars that are flat or rounded. In one embodiment, the first and second articulation drive members 110a and 110b, respectively, are configured to be disposed within the elongated body portion 14.

The drive plates 112a and 112b may be coupled orthogonally to the respective drive members 110a and 110b. The drive plates 112a and 112b may be configured as rectangular plates each having at least a distal engaging aperture 114a, 114b or a proximal engaging aperture 116a, 116b, respectively, formed therein. Each aperture 114a, 114b, and 116a, 116b defines an inner surface 118a, 118b and 120a, 120b, respectively.

The articulation mechanism 100 may further include an articulation drive bar 130 that is configured to contact the drive plates 112a and 112b, such that upon contacting the drive plates 112a and 112b, movement of the articulation drive bar 130 effects movement of the drive plates 112a and 112b to effect the movement of the tool assembly 17.

In one embodiment, the articulation drive bar 130 is configured to engage at least the distal or proximal engaging apertures 114a, 114b or 116a, 116b, respectively, of each of the first and second drive plates 112a and 112b, respectively, such that upon engaging at least the distal or proximal engaging apertures 114a, 114b and 116a, 116b, thereby, movement of the articulation drive bar 130 effects movement of the tool assembly 17.

The articulation drive bar 130 is configured to contact the inner surfaces 118a, 118b, 120a, 120b of at least the distal or proximal engaging apertures 114a, 114b or 116a, 116b, respectively, of each of the drive plates 112a, 112b such that upon contacting the inner surfaces 118a, 118b, 120a, 120b thereby, movement of the articulation drive bar 130 effects movement of the tool assembly 17.

Figure 4:
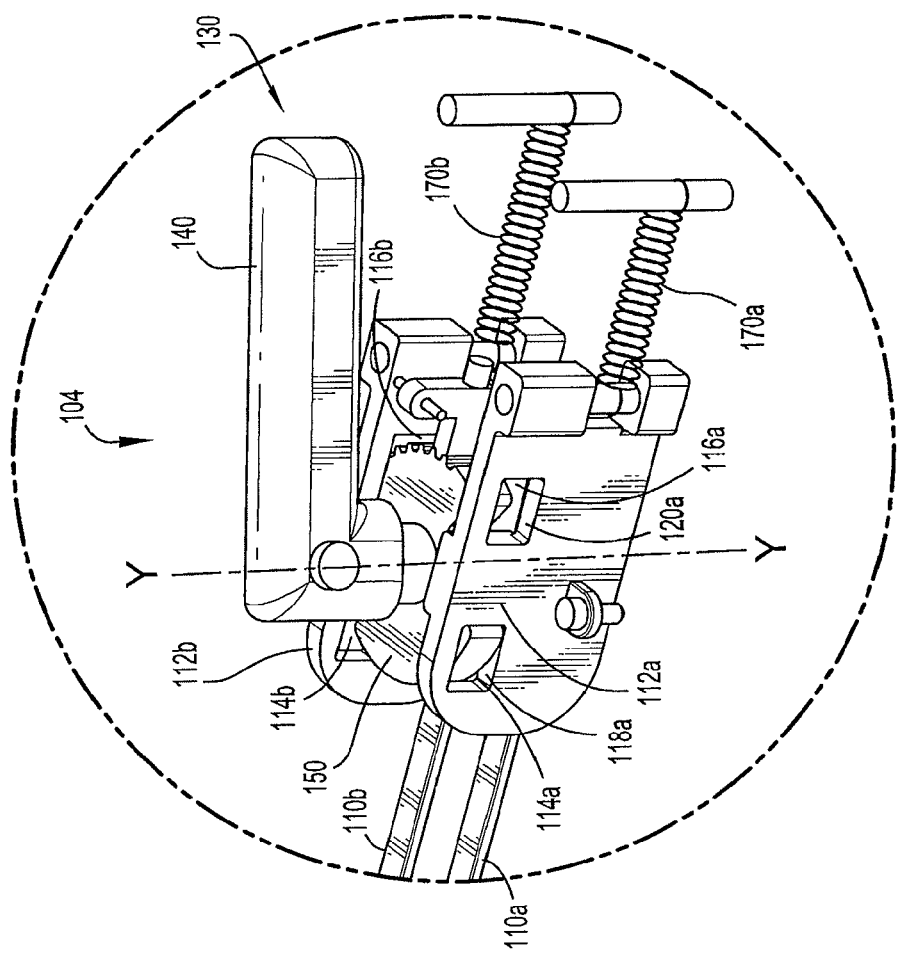
FIG. 4 is a detail of FIG. 2 showing the drive members and other features according to the present disclosure.
Figure 3:
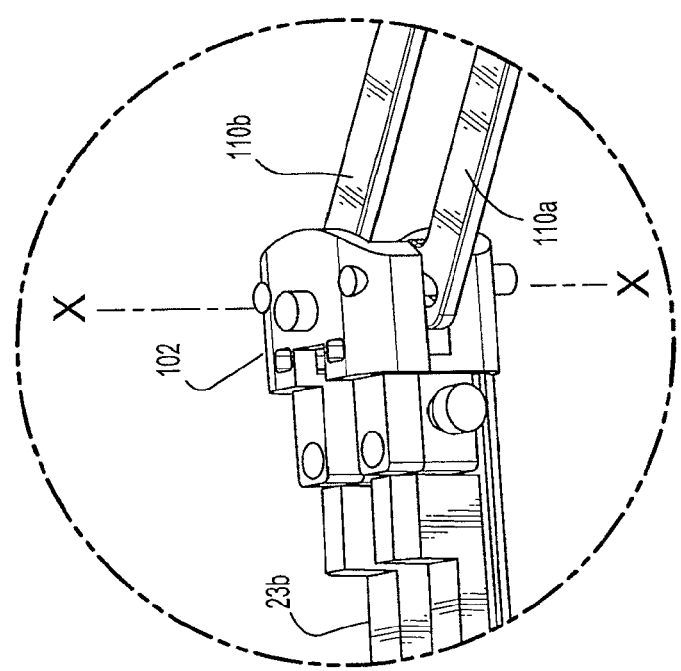
FIG. 3 is a detail of FIG. 2 showing a pivot member and articulation drive members according to the present disclosure.
Figure 5:
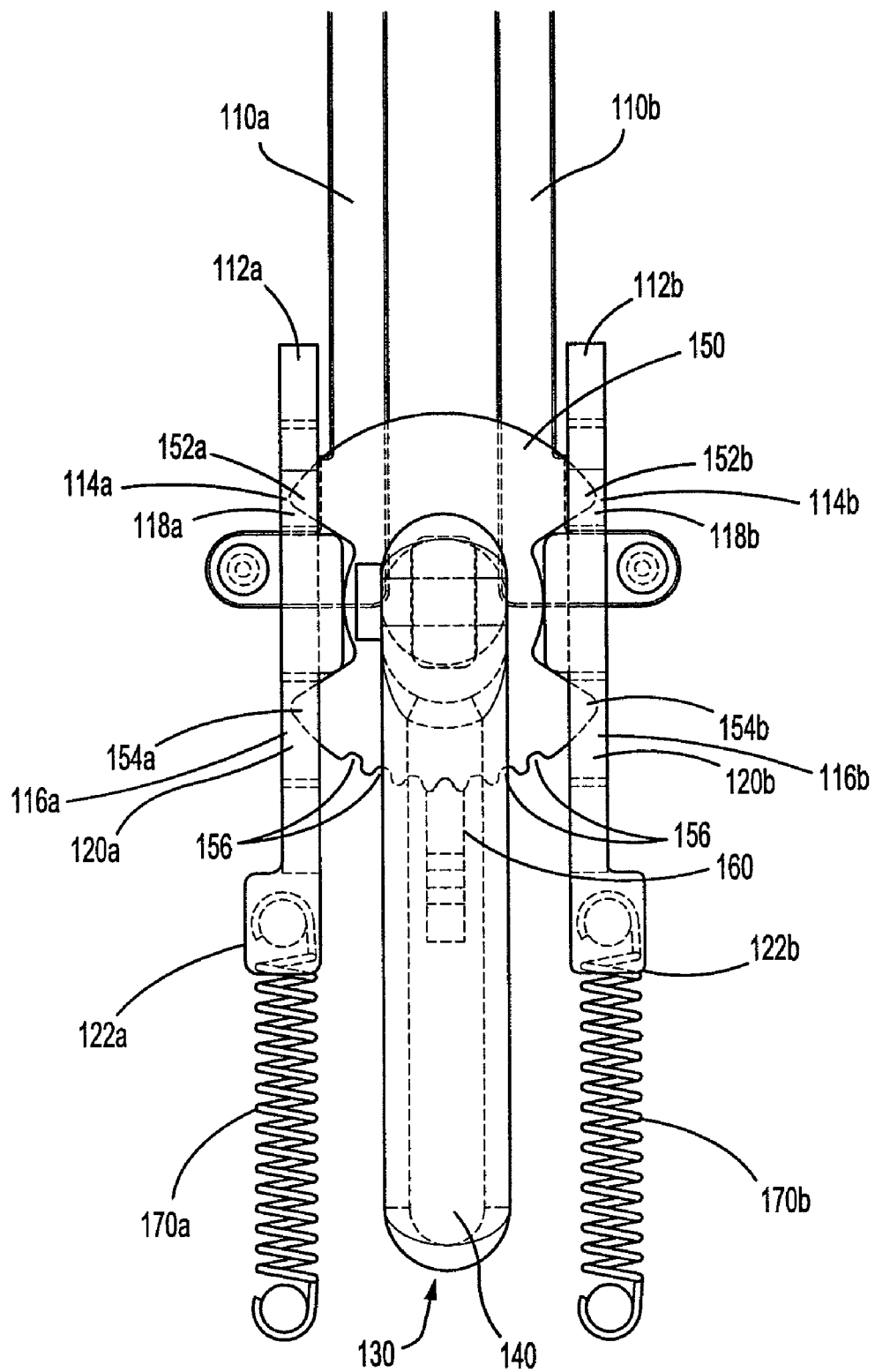
FIG. 5 is a plan view of the proximal end of the articulation mechanism according to the present disclosure illustrating the drive members.

The articulation drive bar 130 may include an operating lever 140 and a base plate 150 that is operatively coupled to the operating lever 140. In one embodiment, as illustrated in FIGS. 2, 4 and 5, the base plate 150 has a bow-tie configuration with four protrusions around the periphery thereof such as first and second pairs each of distal engaging portions 152a and 152b and proximal engaging portions 154a and 154b, respectively. The distal engaging portions 152a and 152b are configured to engage the distal engaging apertures 114a and 114b, respectively, upon movement of the operating lever 140, while the proximal engaging portions 154a and 154b are configured to alternately engage the proximal engaging apertures 116a and 116b, respectively, upon movement of the operating lever 140.

Referring to FIG. 5, the base plate 150 may further include a plurality of notches 156 disposed at the proximal portion of the periphery of the base plate 150. Each of the plurality of notches 156 corresponds to a particular position of the base plate 150 as it is rotated around a vertical centerline axis Y-Y to effect a particular position of articulation of the pivot member 102. Axis Y-Y is shown in FIG. 4, a locking actuator, e.g., locking pin 160, engages with one of the plurality of notches 156 in the base plate 150 to define a predetermined articulated position of the tool assembly 17.

The surgical apparatus 10 may further include a tensioner, e.g., coil springs 170a and 170b, operatively coupled to the surgical apparatus 10, e.g., at the proximal ends 122a and 122b of the first and second articulation drive plates 112a and 112b, respectively, such that the tensioner provides tension to the relative movement of the articulation drive members 110a and 110b.

The articulation drive members 110a, 110b, the articulation drive plates 112a, 112b and the articulation drive bar 130 of the articulation mechanism 100 and associated components may be made from materials such as plastic, metal or metal alloy, or other suitable material.

In operation, the user engages the operating lever 140, turning it to the left or right. When the user turns the operating lever 140 to the right, from the perspective of the user, as shown in FIGS. 1 and 5, proximal engaging portion 154b advances second articulation drive plate 112b in a distal direction. The base plate 150 may also be arranged so that distal engaging portion 152a retracts first articulation drive plate 112a in a proximal direction, as drive plate 112b is advanced. Pivot member 102 pivots so that the tool assembly 17 articulates to the left, as shown in FIG. 1.

As can be appreciated from the above description, the present disclosure provides an articulating endoscopic surgical instrument 10 that includes elongate body portion 14. The elongate body portion 14 defines first longitudinal axis A-A (see FIG. 1). The endoscopic surgical instrument 10 also includes articulating tool assembly 17 that has the pair of jaws 23a and 23b (shown in FIG. 1 in the closed position). The articulating tool assembly 17 defines a second longitudinal axis B-B (see FIG. 1). The articulating tool assembly 17 is disposed at a distal end 19 of the body portion 14 and is movable from a first position in which the second longitudinal axis B-B is substantially aligned with the first longitudinal axis A-A to at least a second position in which the second longitudinal axis B-B is disposed at an angle θ to the first longitudinal axis A-A. The articulating endoscopic instrument 10 also includes the articulation mechanism 100 and the tool assembly 17 that is operatively coupled to the pivot member 102 to effect articulation of the tool assembly 17.

The pivot member 102 is pivotably attached to the elongate body portion 14 at the pivot axis Y-Y (see FIG. 4). The first articulation drive member 110a and the second articulation drive member 110b are attached to the pivot member 102 so that relative movement of the articulation drive members 110a, 110b articulates the tool assembly 17. The first articulation drive member 110a is attached to the pivot member 102 on a first side of the pivot axis X-X and the second articulation drive member 110b is attached to the pivot member 102 on a second side of the pivot axis X-X.

The actuation assembly 104, including the rotatably mounted base 150, is operatively associated with the first and second articulation drive members 110a and 110b, respectively, so that upon rotation of the operating lever 140, the first articulation drive member 110a moves in a proximal direction and the second articulation drive member 110b moves in a distal direction.

Figure 6:
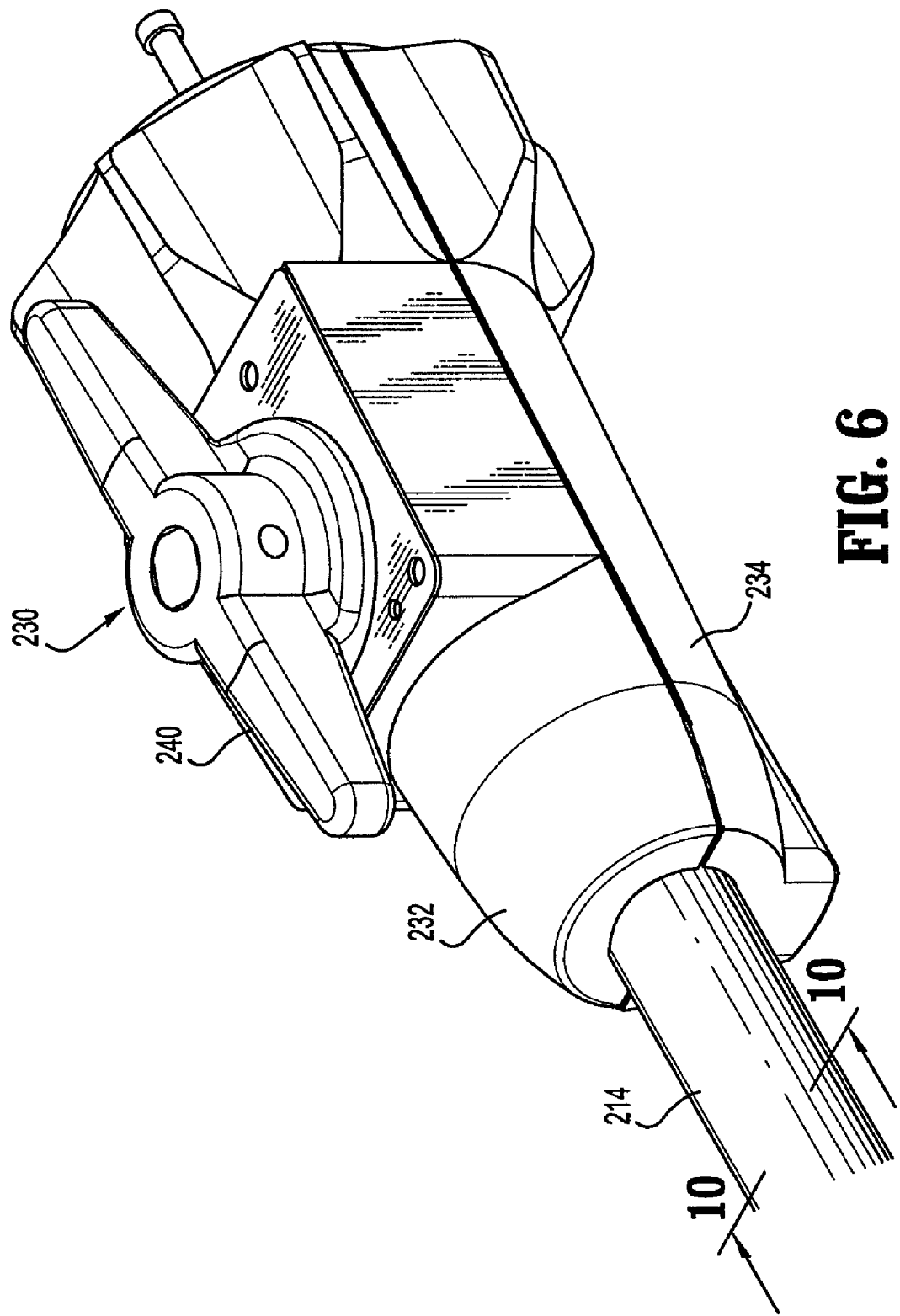
FIG. 6 is a perspective view of an articulation operating mechanism and an elongated body portion for an elongate surgical instrument that both enclose an articulation locking mechanism according to the present disclosure.

Referring now to FIGS. 6-21, there is disclosed an embodiment of an articulation locking mechanism for an articulating elongate surgical instrument. In FIGS. 6-21, only those portions of the articulating surgical instrument are illustrated as necessary to describe the articulation locking mechanism construction and operation. More particularly, referring to FIG. 6, an articulation operating assembly 230 for an elongate surgical instrument includes a pair of upper and lower sections 232 and 234 housing an elongated body portion 214 operatively coupled to the housing (not shown) of the elongate surgical instrument (not shown).

FIG. 7 is a perspective view with parts separated of the internal components of the elongated body portion 214. The elongated body portion 214 includes at least one articulation drive member having at least one retaining surface therein, e.g., first and second articulation drive members 210a and 210b, respectively, each having a retaining surface 205a and 205b, respectively, therein. A firing rod 216 may be disposed adjacent to the articulation drive member or members, e.g., the firing rod 216 may be disposed adjacent to the first articulation drive member 210a and adjacent to the second articulation drive member 210b. An actuating surface 250, may be disposed upon the firing rod 216.

The elongated body 214 also includes an articulation locking means or articulation locking assembly 260 that is configured to selectively engage and disengage from the actuating surface 250 and to selectively engage and disengage from the at least one retaining surface of the at least one articulation drive member, e.g., retaining surface 205a and 205b selectively engaging and disengaging from the articulation drive members 210a and 210b, respectively.

The articulation locking means 260 may be configured to selectively engage and disengage from the actuation surface 250 and with the at least one retaining surface of the articulation drive members, e.g., with the retaining surfaces 205a and 205b of the articulation drive members 210a and 210b, respectively. The articulation locking means 260 includes two retaining surfaces 265a and 265b that selectively engage and disengage from the retaining surfaces 205a and 205b of the respective articulation drive members 210a and 210b.

The retaining surfaces, e.g., retaining surfaces 265a and 265b, of the articulation locking means 260 may be configured as protrusions, wherein each of the protrusions 265a and 265b selectively engages and disengages from the respective retaining surfaces 205a and 205b, of the articulation drive members 210a and 210b, respectively.

Figure 18:
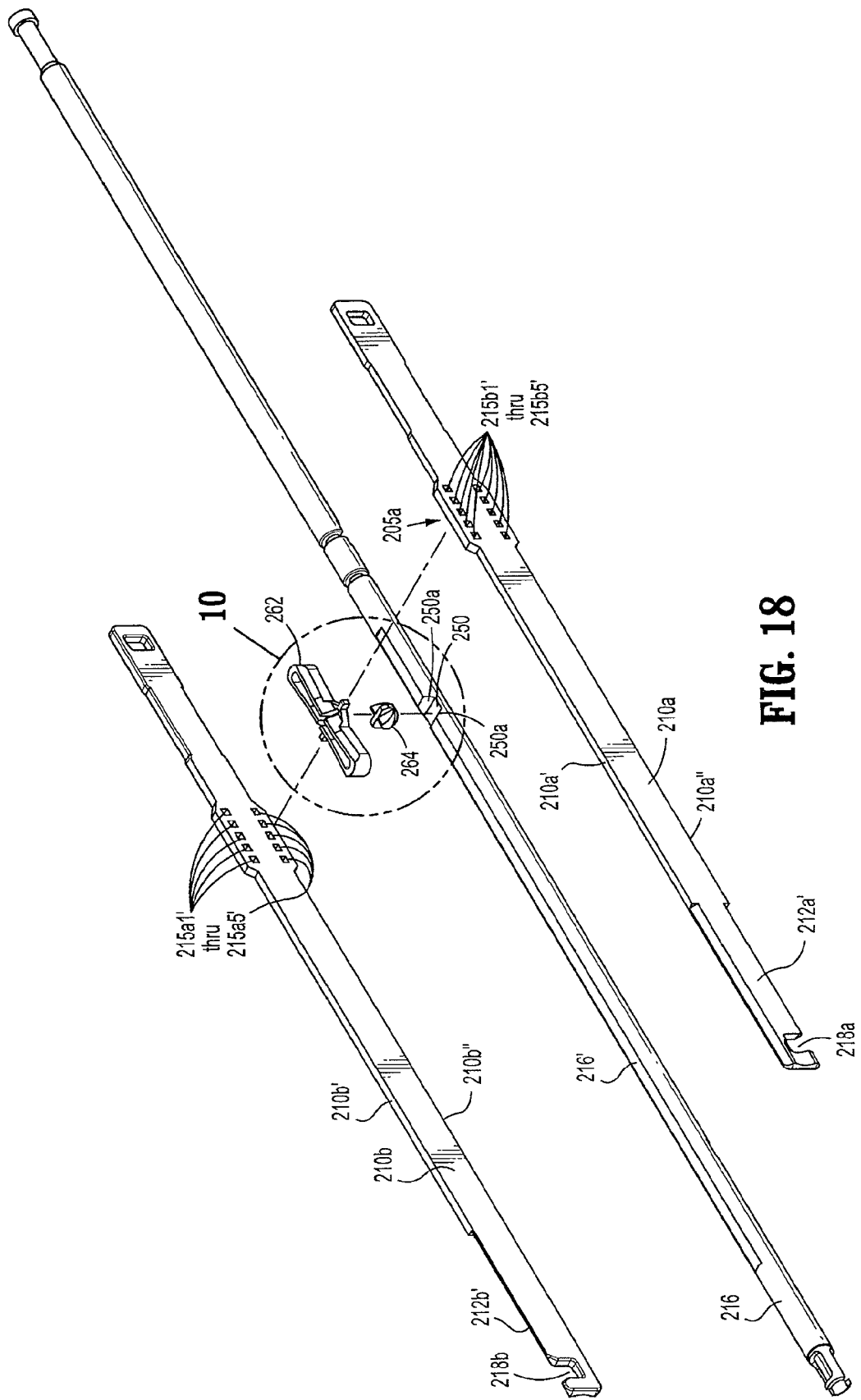
FIG. 18 is a perspective view of the internal components of the elongated body portion, showing an alternate configuration of articulation drive member retaining surfaces.

In one embodiment, retaining surfaces 205a and 205b of the articulation drive members 210a and 210b, respectively, include at least two retaining surfaces, e.g., retaining surfaces 215a1, 215a2, 215a3, 215a4, 215a5 and 215b1, 215b2, 215b3, 215b4, 215b5, respectively. The retaining surfaces, e.g., retaining surfaces 215a1, 215a2, 215a3, 215a4, 215a5 and 215b1, 215b2, 215b3, 215b4, 215b5, respectively, may each be configured as channels receiving the respective protrusions 265a and 265b of the articulation locking means 260. The retaining surfaces 215a1, 215a2, 215a3, 215a4, 215a5 may be disposed on at least one of an upper edge 210a' and a lower edge 210a" of the articulation drive member 210a while the retaining surfaces 215b1, 215b2, 215b3, 215b4, 215b5 may be disposed on at least one of an upper edge 210b' and a lower edge 210b" of the articulation drive member 210b. The articulation drive member channels 215a1, 215a2, 215a3, 215a4, 215a5 and 215b1, 215b2, 215b3, 215b4, 215b5 may be configured as at least one of open channels, as illustrated in FIG. 7, and as closed channels 215a1', 215a2', 215a3', 215a4', 215a5' and 215b1', 215b2', 215b3', 215b4', 215b5', as illustrated in FIG. 18, or may have other shapes. In certain embodiments, retaining surfaces are provided only on one of the upper or lower edges of the articulation drive members. In other embodiments, retaining surfaces are provided on both edges, to provide symmetry for manufacturing purposes, or for engagement by a second locking means.

Figure 8B:
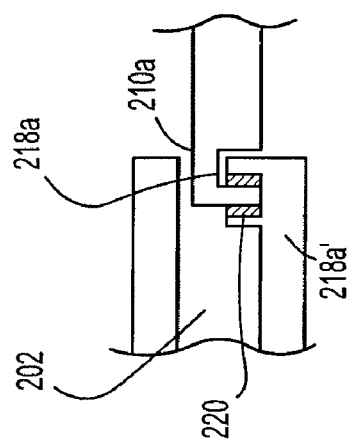
FIG. 8B is a side view of the pivot member and an articulation drive member of the elongated body portion of FIG. 8A.
Figure 8C:
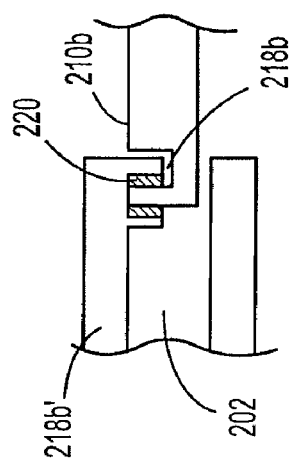
FIG. 8C is a side view of the pivot member and another articulation drive member of the elongated body portion of FIG. 8A.
Figure 8A:
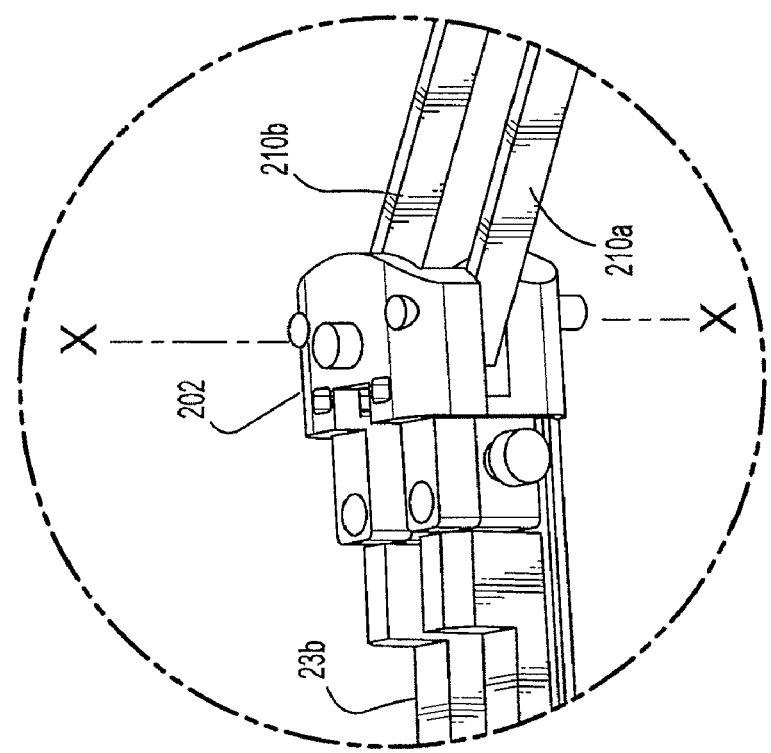
FIG. 8A is a perspective view showing one embodiment of a pivot member and articulation drive members of the elongated body portion for an elongate surgical instrument of FIG. 6.

FIG. 7 also illustrates that the drive members 210a and 210b each include a proximal end 212a and 212b, respectively, and a distal end 212a' and 212b', respectively. At the distal ends 212a' and 212b', there is disposed a pivot engaging joint 218a and 218b, respectively, that is illustrated in FIGS. 7, 8A and 8B as being exemplified by a U-shaped loop joint.

At distal end 212a', the elongated body member 214 includes a pivot member 202 that is operatively coupled to an anvil assembly, such as anvil assembly 23a (see FIG. 1) and cartridge assembly 23b (see FIGS. 1-3 and 8A). The anvil assembly 23a is movably secured in relation to elongated body 214.

The pivot engaging joints 218a and 218b are disposed within the pivot member 202 to connect the drive members 210a and 210b to the pivot member 202. A pivot engaging joint 218a' is configured in an inverted U-shaped loop so as to engage with the vertical U-shaped loop of pivot engaging joint 218a via a sleeve 220, while a pivot engaging joint 218b' is configured in a vertical U-shaped loop so as to engage with the inverted U-shaped loop of pivot engaging joint 218b via another sleeve 220 (see FIGS. 8B and 8C).

Figure 9B:
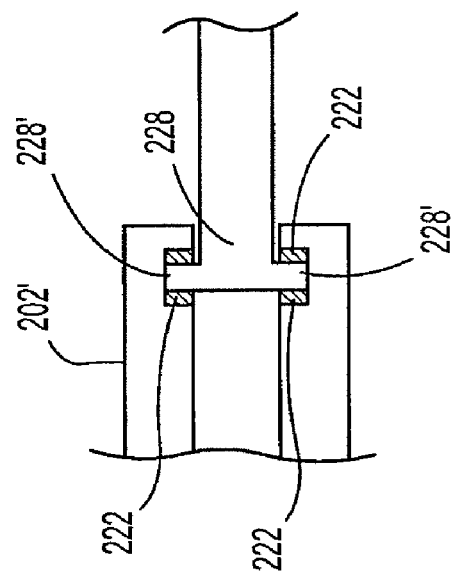
FIG. 9B is a side view of the pivot member and articulation drive members of the elongated body portion of FIG. 9A.
Figure 9A:
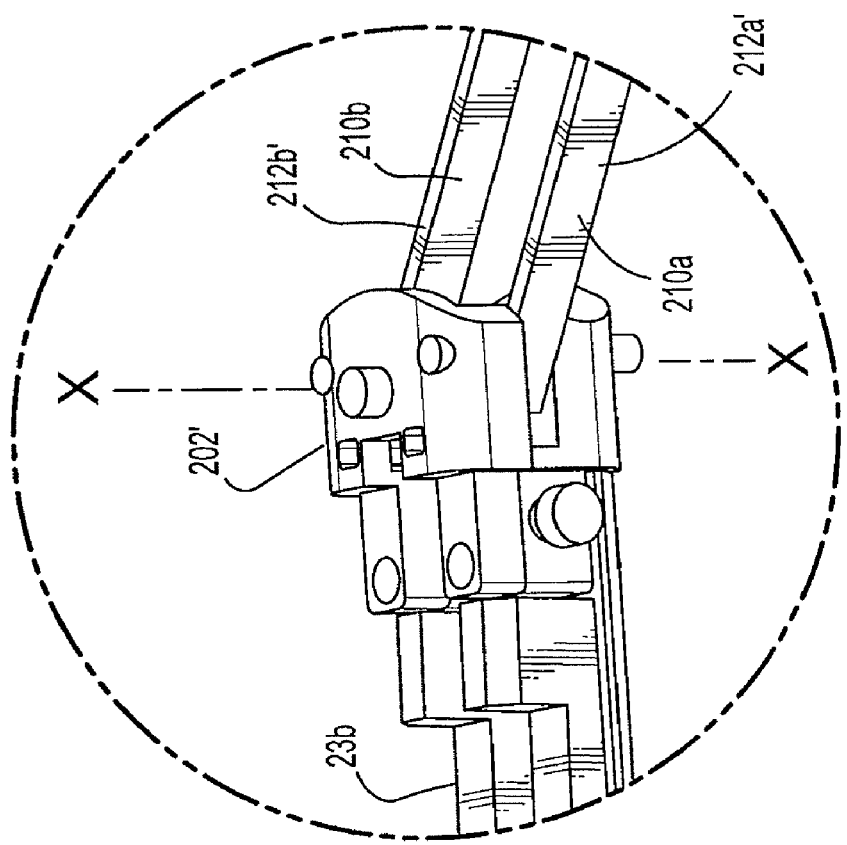
FIG. 9A is a perspective view showing another embodiment of a pivot member and articulation drive members of the elongated body portion for an elongate surgical instrument of FIG. 6.
Figure 10:
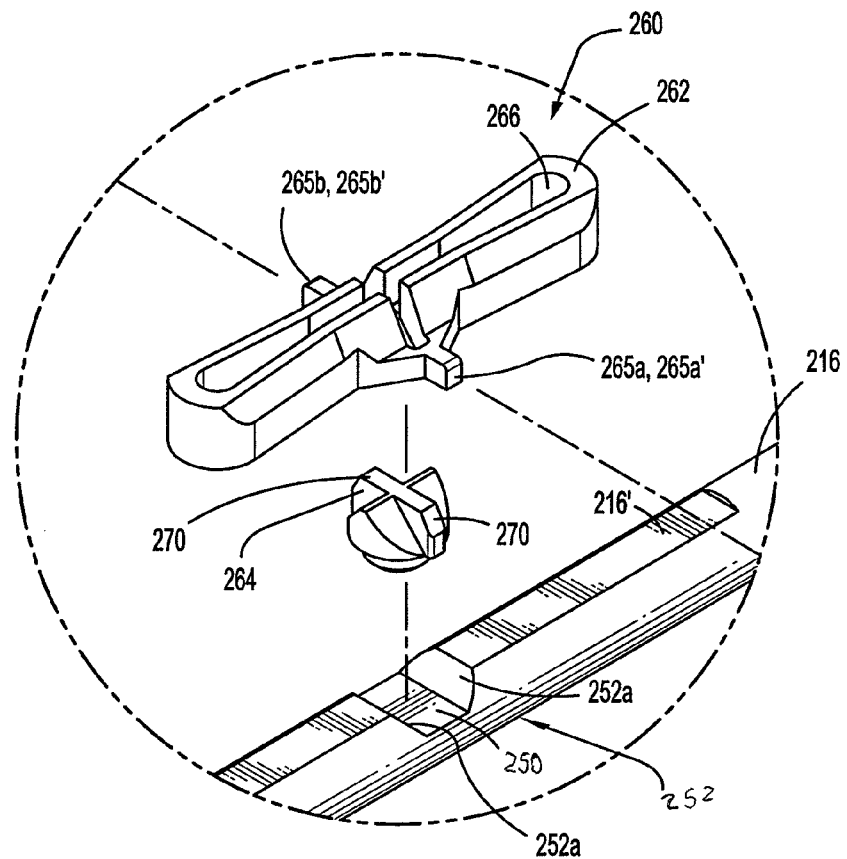
FIG. 10 is a perspective view with parts separated of internal components of the elongated body portion of the elongate surgical instrument of FIG. 8 illustrating one embodiment of an articulation locking mechanism according to the present disclosure.
Figure 11:
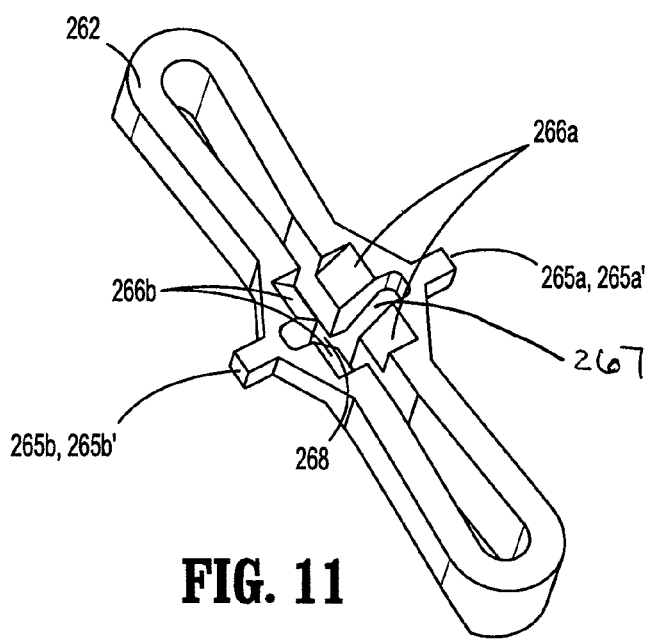
FIG. 11 is a perspective view of the articulation locking mechanism of FIG. 10.
Figure 12:
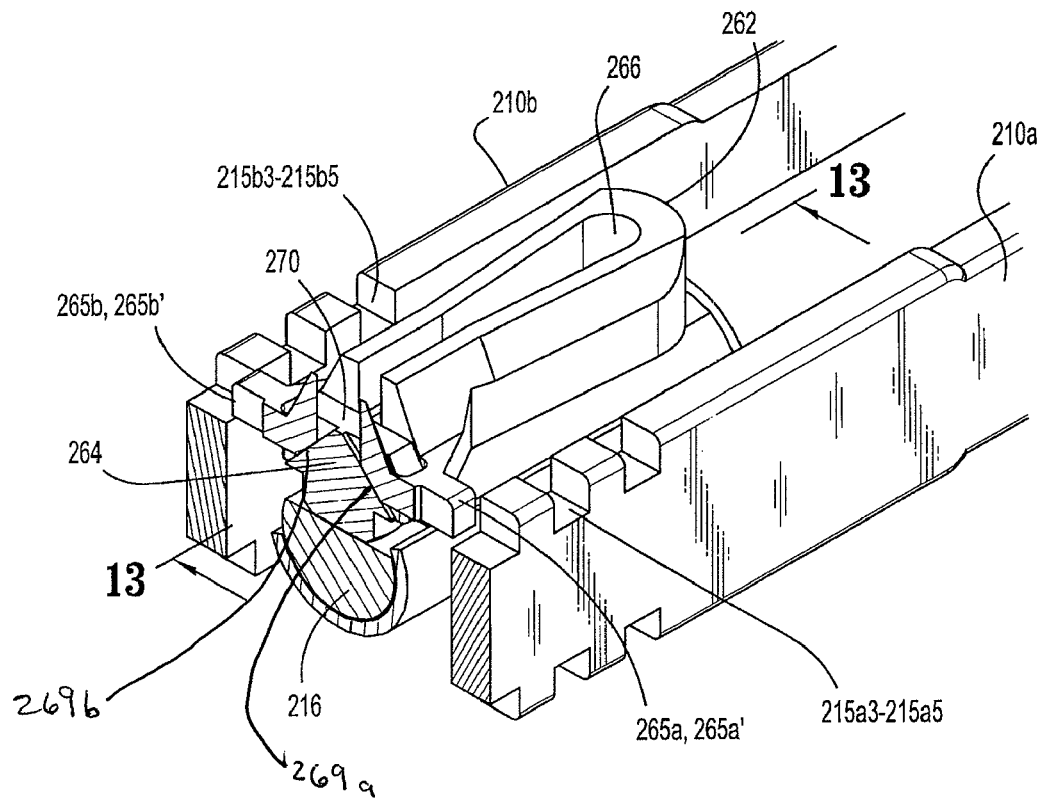
FIG. 12 is a sectional perspective view of the internal components of the elongated body portion of FIGS. 6, 7 and 10.
Figure 13:
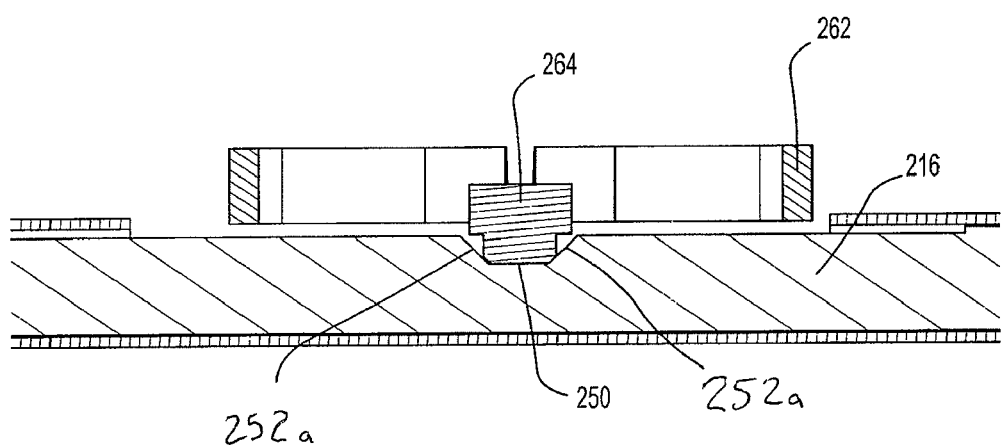
FIG. 13 is another sectional view of the internal components of the elongated body portion, taken along line 13-13 in FIG. 12, showing the articulation locking mechanism in a disengaged position.
Figure 14:
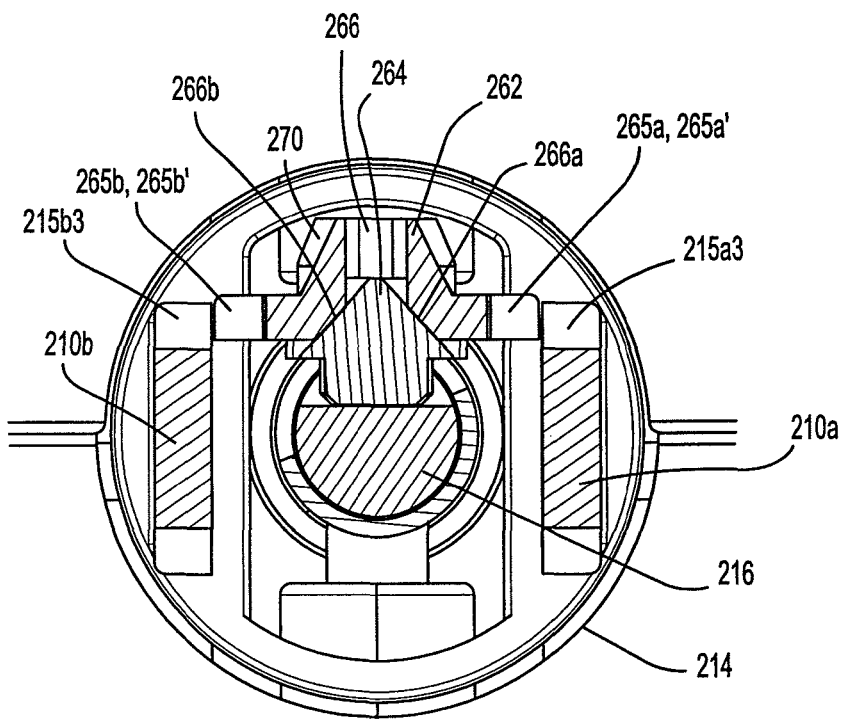
FIG. 14 is a cross-sectional view of the internal components of the elongated body portion of FIGS. 10, 11 and 13 showing the articulation locking mechanism in a disengaged position.
Figure 15:
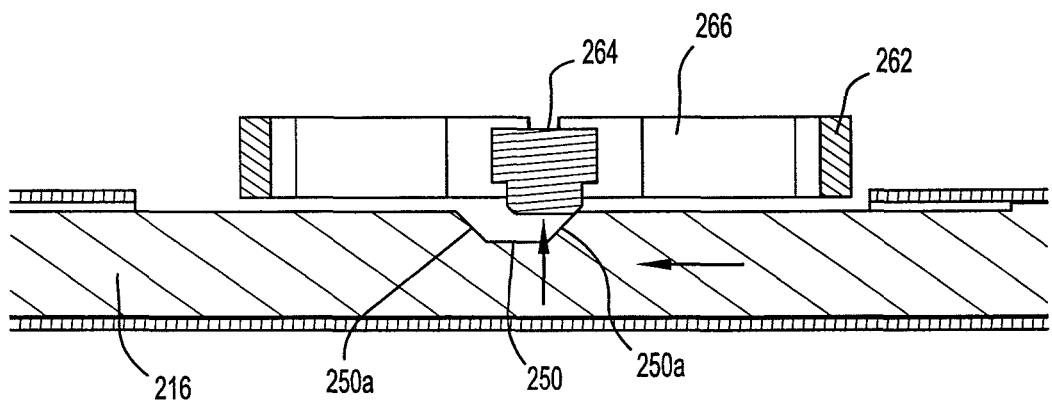
FIG. 15 is a sectional view of the internal components of the elongated body portion of FIGS. 10, 11, 13 and 14 showing the articulation locking mechanism in an engaged position.
Figure 16:
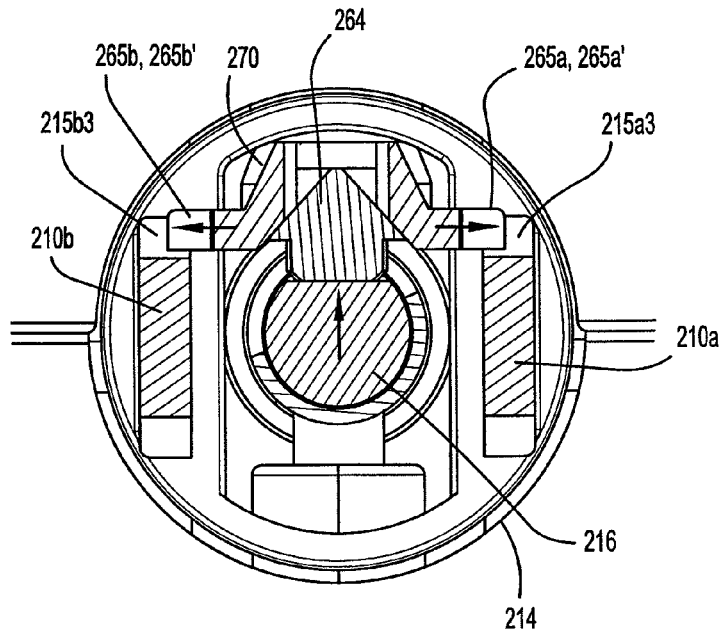
FIG. 16 is a cross-sectional view of the internal components of the elongated body portion of FIGS. 10, 11, 13, 14 and 15 showing the articulation locking mechanism in an engaged position.
Figure 17:
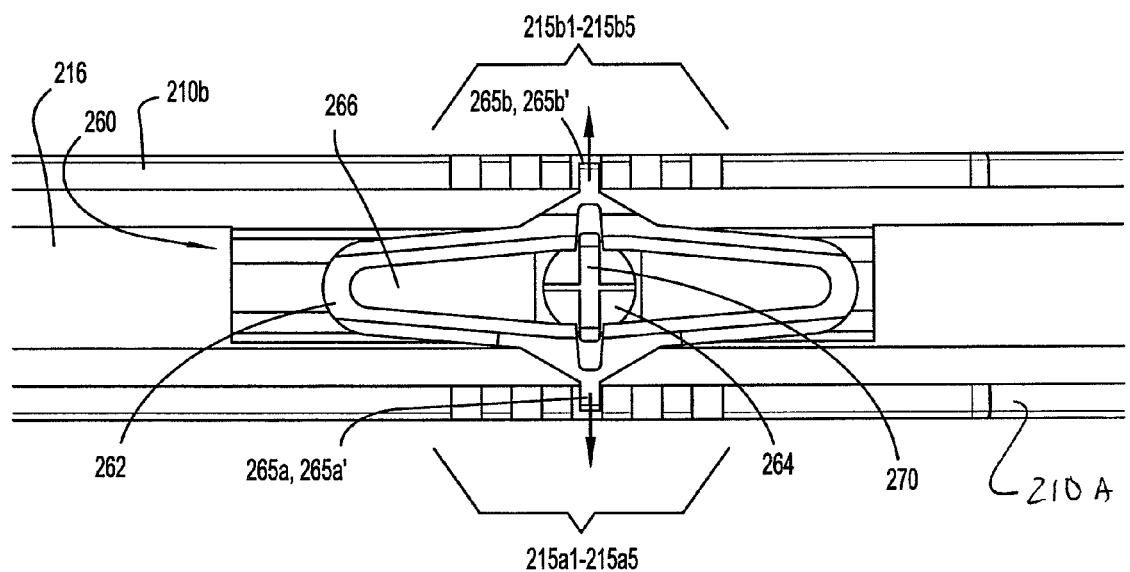
FIG. 17 is a plan view of the internal components of the elongated body portion of FIGS. 10, 11, 13, 14, 15 and 16 showing the articulation locking mechanism in an engaged position.

FIGS. 9A and 9B illustrate an alternate configuration of the pivot member 202 and of the distal ends 212a' and 212b' of drive members 210a and 210b. More particularly, distal ends 212a" and 212b" of drive members 210a and 210b pivot member 202' are each configured with pivot engaging joints 228a and 228b, respectively, having a T-shaped configuration having arms 228' of the T-shape. A pivot member 202' is configured with sleeves 222 that are disposed in the pivot member 202' to receive the arms 228' of the T-shaped distal ends 212a" and 212b", respectively.

Figure 19:
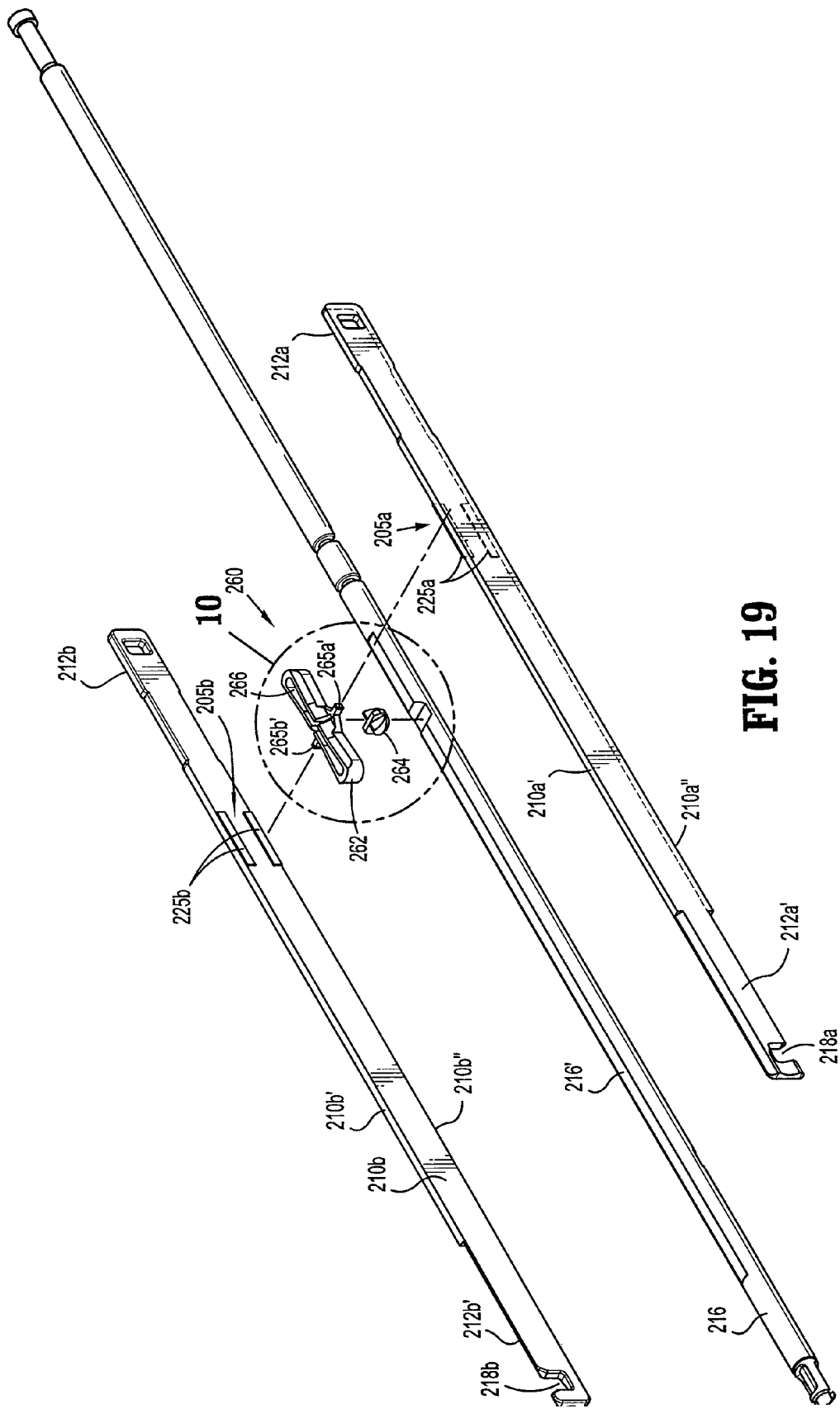
FIG. 19 is a perspective view of the internal components of the elongated body portion, showing an alternate configuration of articulation drive member retaining surfaces.
Figure 20:
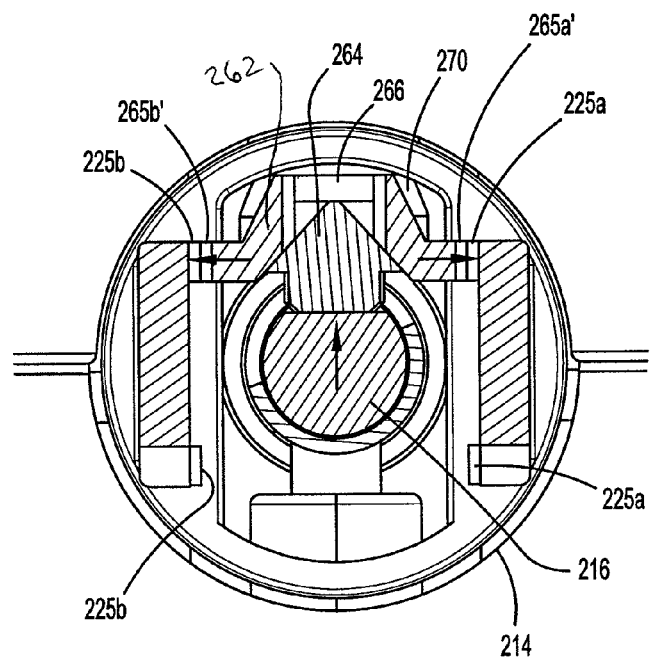
FIG. 20 is a cross-sectional view of the internal components of the elongated body portion of FIG. 19 showing the articulation drive member retaining surfaces in an engaged position.
Figure 21:
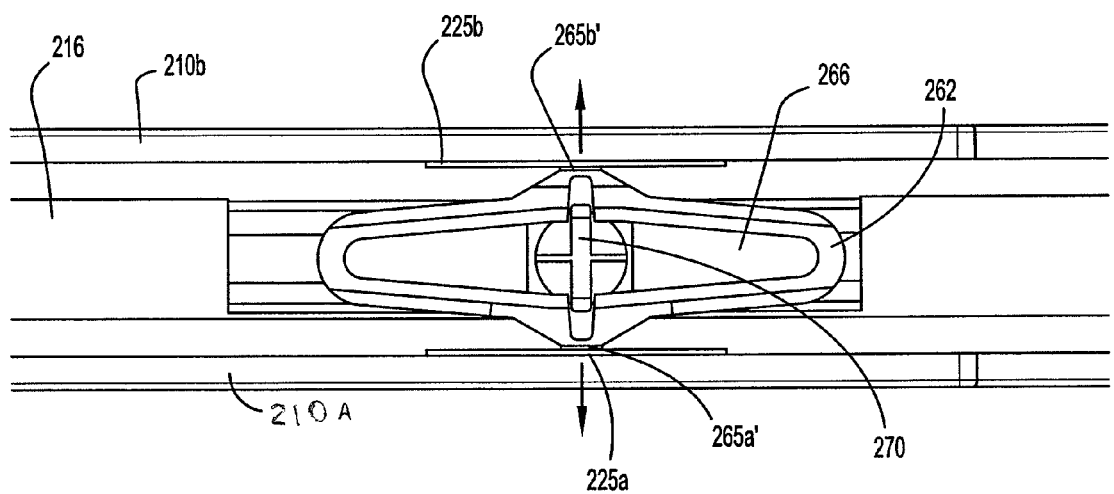
FIG. 21 is a plan view of the internal components of the elongated body portion of FIGS. 19 and 20 showing an alternate configuration of articulation drive member retaining surfaces in an engaged position.

Referring to FIGS. 19-21, in one embodiment, the retaining surfaces of the articulation locking means, e.g., retaining surfaces 265a and 265b of the articulation locking means 260, may each include a frictional surface. Frictional surfaces 265a' and 265b', respectively, selectively engage and disengage from the retaining surfaces 205a and 205b of the articulation drive members 210a and 210b, respectively. The frictional surfaces 265a' and 265b' selectively engage and disengage with respective frictional surfaces 225a and 225b. The frictional surfaces 265a', 265b' and 225a, 225b are formed from a material or are textured to increase friction between the drive members and the locking means 260 and resist movement of the drive members 210a and 210b.

As best shown in FIGS. 10-17, the articulation locking means 260 is configured to selectively engage and disengage from the actuating surface 250 and selectively engage and disengage from retaining surfaces 205a and 205b of articulation drive members 210a and 210b, respectively.

The articulation locking means 260 may include a motive member, e.g., a plunger 264, that is configured to selectively engage and disengage from a flexible member 262, or interact with the flexible member 262, to effect engagement and disengagement of the retaining surfaces 265a and 265b from the retaining surfaces 205a and 205b of drive members 210a and 210b, respectively.

The actuating or actuation surface 250 and the motive member 264 may be configured wherein motion of a component within the elongate body 214 effects motion of the motive member 264. The actuating surface 250 of firing rod 216 may be configured as a detent channel 252 in a surface 216' of the firing rod 216. The detent channel 252 includes at least one ramp surface 252a configured to urge movement of the motive member 264 upon motion of the firing rod 216.

The flexible member 262 may be configured in a loop-type arrangement having an interior space 266. Upon motion of the firing rod 216, the motive member 264 enters the interior space 266 and is urged towards the flexible member 262 and interacts with the flexible member 262 so as to move protrusions 265a and 265b towards the drive members 210a and 210b.

The flexible member 262 includes inclined surfaces 266a and 266b spanning the interior space 266. The firing rod 216 is moved forward, so that motive member 264 rides up out of channel 252. When motive member 264 rests on surface 216' (see FIG. 10), the flexible member 262 is engaged with the drive members 210a and 210b. The motive member 264 is arranged and configured to laterally expand the sides of the flexible member 262. The motive member 264 has inclined surfaces 269a, 269b that engage the inclined surfaces 266a and 266b of the flexible member 262 so that as the motive member 264 is urged towards the flexible member 262, the sides of flexible member 262 (which carry protrusions 265a and 265b) are cammed laterally towards the drive members 210a and 210b. The protrusions 265a and 265b engage retaining surfaces 205a and 205b. Guidance rib 270 on the motive member 264 prevents longitudinal movement of the motive member 264, through engagement with slot 267 in the flexible member 262.

The flexible member 262 is preferably configured to have sufficient resiliency to urge the motive member 264 away from the flexible member 262, thereby releasing the drive members 210a and 210b and allowing movement thereof. When the firing rod 216 is retracted, the motive member 264 will align with the channel 252, allowing the motive member 264 to move away from the flexible member 262. The resilient nature of the flexible member 262 moves the sides of the flexible member 262 inwardly, moving the retaining surfaces 265a, 265b away from retaining surfaces 205a, 205b. The firing rod 216 can be a rod for actuating the firing of the staples or a rod dedicated to locking the position of the tool assembly 17. In certain alternative embodiments, the firing rod 216 has an actuating feature 250 that is formed as a protrusion on the firing rod 216. When the firing rod 216 is moved, the motive member 264 rides up on a ramp surface of the protrusion, engaging the flexible member 262.

As can be appreciated, the embodiments of the articulation mechanism 100 and the articulation locking means 260 and the associated components within the elongated body 214, described above, may be applied to surgical instruments other than a stapling apparatus. Examples include grasping instruments or retractors.

In further embodiments, one articulation drive member 210 is provided and the articulation locking means has retaining surfaces on one side, arranged to engage retaining surfaces on the articulation drive member.

In certain embodiments, the tool assembly 17 is provided as a removable and replaceable assembly attached to the elongate body portion 14. The tool assembly 17 and a housing portion that attaches to the elongate body portion 14 form a loading unit that includes one or more links that connect with the one or more drive members of the articulation assembly.

Although the subject disclosure has been described with respect to exemplary embodiments, it will be readily apparent to those having ordinary skill in the art to which it appertains that changes and modifications may be made thereto without departing from the spirit or scope of the subject disclosure as defined by the appended claims.

What is claimed is:

1. A method of preventing articulation in a surgical instrument comprising a firing rod having an actuating surface thereon and a firing direction, the surgical instrument defining an elongated body, the firing rod firing surgical staples from a tool assembly in a direction of firing upon an actuation of the surgical instrument the tool assembly being pivotally supported on a distal end of the elongated body, the method comprising moving the firing rod so that the actuating surface engages an articulation locking assembly having a flexible member such that the flexible member is moved laterally with respect to the firing direction to engage at least one articulation drive member.

2. The method of claim 1, further comprising engaging a motive member with the firing rod, the actuating surface urging movement of the motive member.

3. The method of claim 2, wherein the motive member is moved toward the flexible member.

4. The method of claim 3, wherein the motive member moves into an interior space of the flexible member, expanding the flexible member laterally with respect to the firing direction.

5. The method of claim 3, further comprising moving the motive member into a channel in the firing rod and away from the flexible member.

6. The method of claim 3, further comprising sliding the motive member along at least one inclined surface.

7. The method of claim 1, further comprising moving retaining surfaces on the flexible member into engagement with retaining surfaces on the at least one articulation drive member.

8. The method of claim 1, further comprising moving the flexible member laterally in two directions with respect to the firing direction to engage two articulation drive members.

9. The method of claim 1, further comprising firing surgical staples from the surgical instrument, including moving the firing rod in a distal direction.

* * * * *